(12) United States Patent
Elkins

(10) Patent No.: US 8,900,170 B1
(45) Date of Patent: Dec. 2, 2014

(54) TEMPERATURE CONTROL HEADLINER

(75) Inventor: William Elkins, Lincoln, CA (US)

(73) Assignee: Welkins, LLC

( * ) Notice: Subject to any disclaimer, the term of this patent is extended or adjusted under 35 U.S.C. 154(b) by 274 days.

(21) Appl. No.: 13/373,061

(22) Filed: Nov. 3, 2011

Related U.S. Application Data

(60) Provisional application No. 61/456,423, filed on Nov. 5, 2010.

(51) Int. Cl.
*A61F 5/00* (2006.01)

(52) U.S. Cl.
USPC .................. 602/2; 602/17; 607/104; 607/109

(58) Field of Classification Search
USPC ............ 602/13, 17–18, 2; 607/104, 109, 110; 2/458
See application file for complete search history.

(56) References Cited

U.S. PATENT DOCUMENTS

| | | | |
|---|---|---|---|
| 6,178,562 B1 * | 1/2001 | Elkins ............................... | 2/458 |
| 6,183,501 B1 | 2/2001 | Latham | |
| 6,277,143 B1 * | 8/2001 | Klatz et al. ..................... | 607/104 |
| 7,052,509 B2 * | 5/2006 | Lennox et al. ................. | 607/109 |
| 7,744,640 B1 * | 6/2010 | Faries et al. .................... | 607/109 |
| 8,454,671 B2 * | 6/2013 | Lennox et al. ................. | 607/104 |
| 2010/0324635 A1 | 12/2010 | Kreck | |

OTHER PUBLICATIONS

PCT, International Search Report and the Written Opinion of the International Searching Authority, in International application No. PCT/US2010/0262558, dated Jan. 22, 2013. (10 pages).

\* cited by examiner

*Primary Examiner* — Michael A. Brown

(74) *Attorney, Agent, or Firm* — McAndrews, Held & Malloy, Ltd.

(57) ABSTRACT

A headliner is provided for controlling a temperature of a head of a patient. A cap is provided which fits securely over the head of the patient. A fluid pathway is routed through the cap with a fluid space adapted to receive heat transfer fluid therein and route the heat transfer fluid between an inlet and an outlet on the cap. The inlet and outlet are each coupled to a cooler for the heat transfer fluid and the heat transfer fluid is circulated through the cap and the cooler such that heat is drawn from the head of the patient. An air bladder is optionally provided outboard of the fluid space which is filled with pressurized gas to increase contact between the fluid space and the head of the patient. A neck brace is integrated with the cap portion of the headliner, particularly for treatment of head trauma.

19 Claims, 11 Drawing Sheets

TEMPERATURE CONTROL HEADLINER

CROSS-REFERENCE TO RELATED APPLICATIONS

This application claims benefit under Title 35, United States Code §119(e) of U.S. Provisional Application No. 61/456,423 filed on Nov. 5, 2010.

FIELD OF THE INVENTION

The following invention relates to devices for treating stroke, head trauma or other brain injury. More particularly, this invention relates to devices for cooling the head of a patient, such as in response to an existing or potential brain injury.

BACKGROUND OF THE INVENTION

Brain function can experience impairment of a temporary or permanent nature as a result of various different brain injuries. Such brain injuries can include stroke, where blood flow to the brain is temporarily blocked. Also, head trauma can cause brain injury. Other sources of brain injury can include heat stroke, where an excessively high temperature is experienced by the brain, aneurysms, and other bleeding disorders, as well as other deleterious brain injury phenomena.

One common feature in treating and successfully recovering from brain injury is the concept that time is critical in treating brain injury. In particular, when brain cells die, the associated function provided by those brain cells is more apt to be lost by the patient. When a sufficient number of brain cells have died, such function is lost, and the potential for the function returning decreases as more and more brain cells die. Hence, it is imperative that the therapy indicated in response to the brain injury be executed as soon as possible after the brain injury occurs to minimize such deleterious effects.

An interesting phenomena has been observed by those who study brain injury relating to the brain cell survival rate as a function of time when brain temperature is reduced. In particular, drowning victims in exceptionally cold water have in some cases been submerged and deprived of oxygen for tens of minutes. While such a time period would ordinarily cause such extensive brain cell loss that significant brain function loss would occur, it has been observed that brain function has in many cases been restored completely, or nearly completely. Based on these observations, it has been determined that by cooling the patient's head, an effect similar to "slowing down the clock" can be achieved. Accordingly, a need exists for extending this observed benefit from accidental occurrences to intentional use of this effect in the beneficial treatment of brain injury, and particularly stroke and head trauma.

SUMMARY OF THE INVENTION

With this invention, a headliner is provided generally in the form of a cap and integrated with a cervical collar. The cap has a pathway routed therethrough which extends from an inlet to an outlet. The cap is formed of at least two layers including an inner layer located adjacent the patient's head and an outer layer spaced further from the patient's head. A fluid space is thus provided between the two layers and along the heat transfer fluid pathway adjacent the patient's head. A source of heat transfer fluid is provided coupled to the inlet and heat transfer fluid is allowed to flow along this pathway. The heat transfer fluid is cooled to below a temperature deemed effective to produce the desired therapeutic result, namely "slowing down the clock" so that brain cell death is minimized until brain injury therapies can be performed. The heat transfer fluid is removed from the cap at an outlet and preferably routed back to a cooler for removal of heat from the heat transfer fluid and recirculation of the re-cooled heat transfer fluid back to the inlet for reuse within the cap.

Most preferably, particularly in the context of head trauma, the headliner also includes a neck brace portion for use in conjunction with the cap portion. The headliner is integrated with the neck brace to allow both components to be simultaneously applied to the head. By integration, there is an additional synergistic integration, stabilizing and positioning of the headliner. Such integration also reduces the time before cooling can be introduced. The neck brace both helps to hold portions of the heat transfer fluid pathway in intimate contact with the patient's head, but also is often desirable for stabilizing of the patient's head when a brain injury has occurred, and to avoid further injury to the cervical structures of the patient.

The cap optionally but preferably includes an air bladder located directly adjacent an exterior side of the fluid space. This air bladder can receive a compressed gas to increase a degree of contact between the fluid space and the patient's head, such that a rate of heat transfer can be maximized. Furthermore, seams are preferably provided on borders on opposite sides of the heat transfer fluid pathway as it is routed over the head of the patient and within the cap. These seams are elastically held closed, tending to draw the cap tightly upon the patient's head and increasing a degree of contact with the patient's head for maximum heat transfer, as well as to provide adjustability for proper fit on patients of different head sizes.

OBJECTS OF THE INVENTION

Accordingly, a primary object of the present invention is to protect a patient's brain from further damage from a moment of brain injury until and during brain injury repair therapy.

Another object of the present invention is to provide a headliner attachable to a head of a wearer for controlling a temperature of the patient's head.

Another object of the present invention is to provide a headliner for increasing a degree of comfort experienced by the wearer.

Another object of the present invention is to "slow down the clock" before, during and after medical procedures are performed, particularly upon a head of a wearer.

Another object of the present invention is to provide a temperature control headliner which can also stabilize cervical structures of the patient.

Another object of the present invention is to provide a temperature control headliner which can fit upon heads of patients which are of different sizes.

Another object of the present invention is to provide a temperature control headliner which can be readily connected and disconnected from a source of heat transfer fluid and a heat transfer fluid cooler, as well as a source of compressed air.

Another object of the present invention is to provide a temperature control headliner which is easy to attach to and fit upon a head of a patient, particularly when the patient is unable to assist in the donning of the headliner.

Another object of the present invention is to reduce the time for installing both the cooling headliner and the cervical collar by simultaneous installation of both elements.

Another object of the present invention is to decrease loss of brain function resulting from a stroke.

Another object of the present invention is to decrease a degree of brain function loss resulting from epilepsy, cardiac arrest, extreme blood pressure, poisoning, heart attack and other conditions where a potential for brain function loss is presented.

Other further objects of the present invention will become apparent from a careful reading of the included drawing figures, the claims and detailed description of the invention.

BRIEF DESCRIPTION OF THE DRAWING FIGURES

Figure 13:
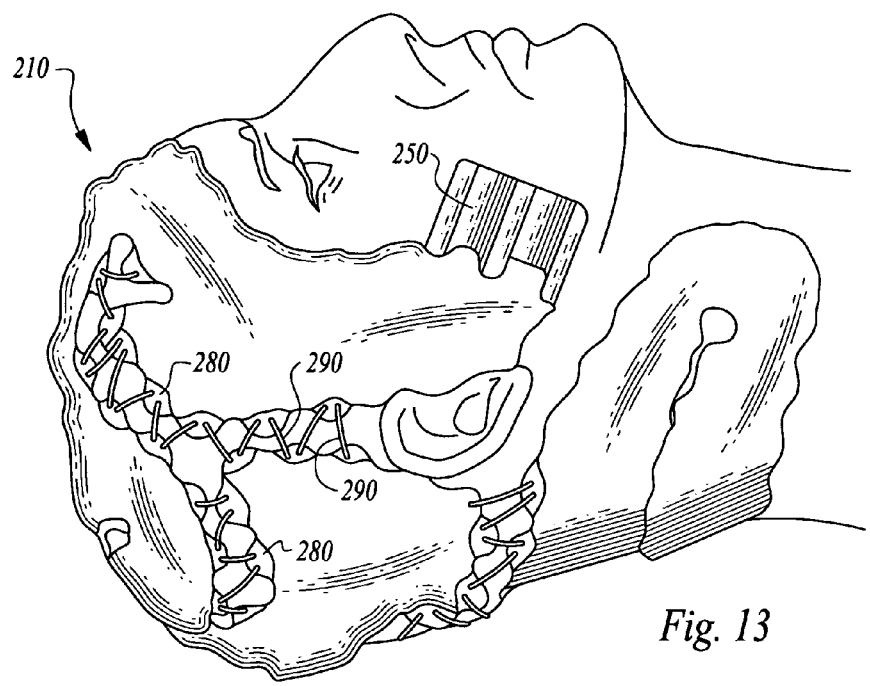
Figure 14:
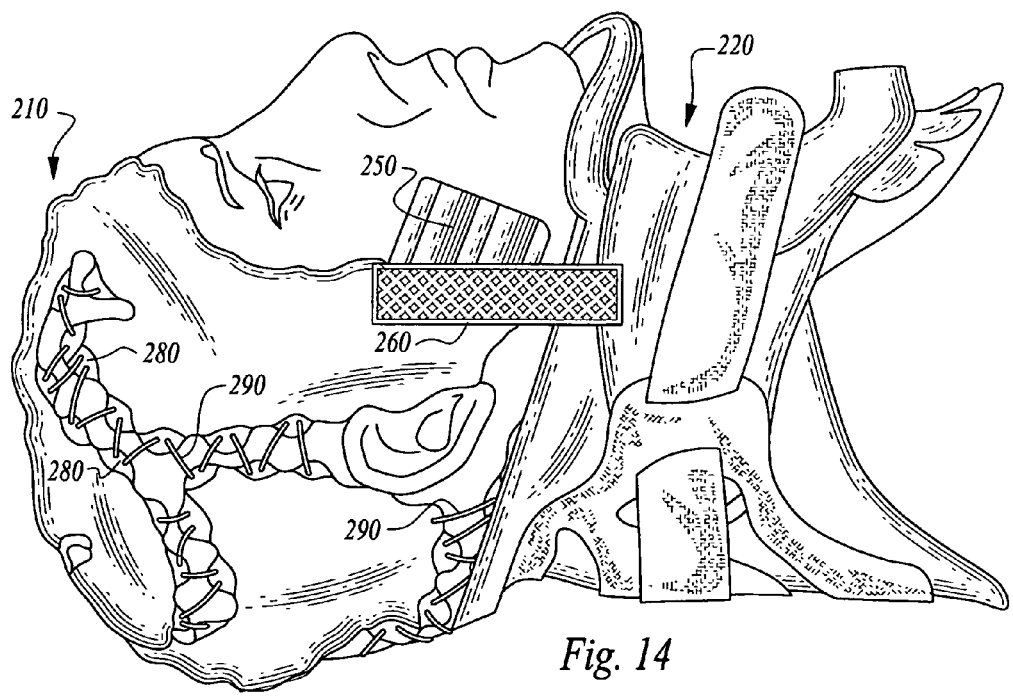

FIGS. 13 and 14 are side elevation views of an embodiment headliner of this invention integrated with a cervical collar, and shown on a model head of a patient. In FIG. 13 the cervical collar portion is removed to show all of the cap details. In FIG. 14 both the integrated headliner and cervical collar are shown together.

Figure 7:
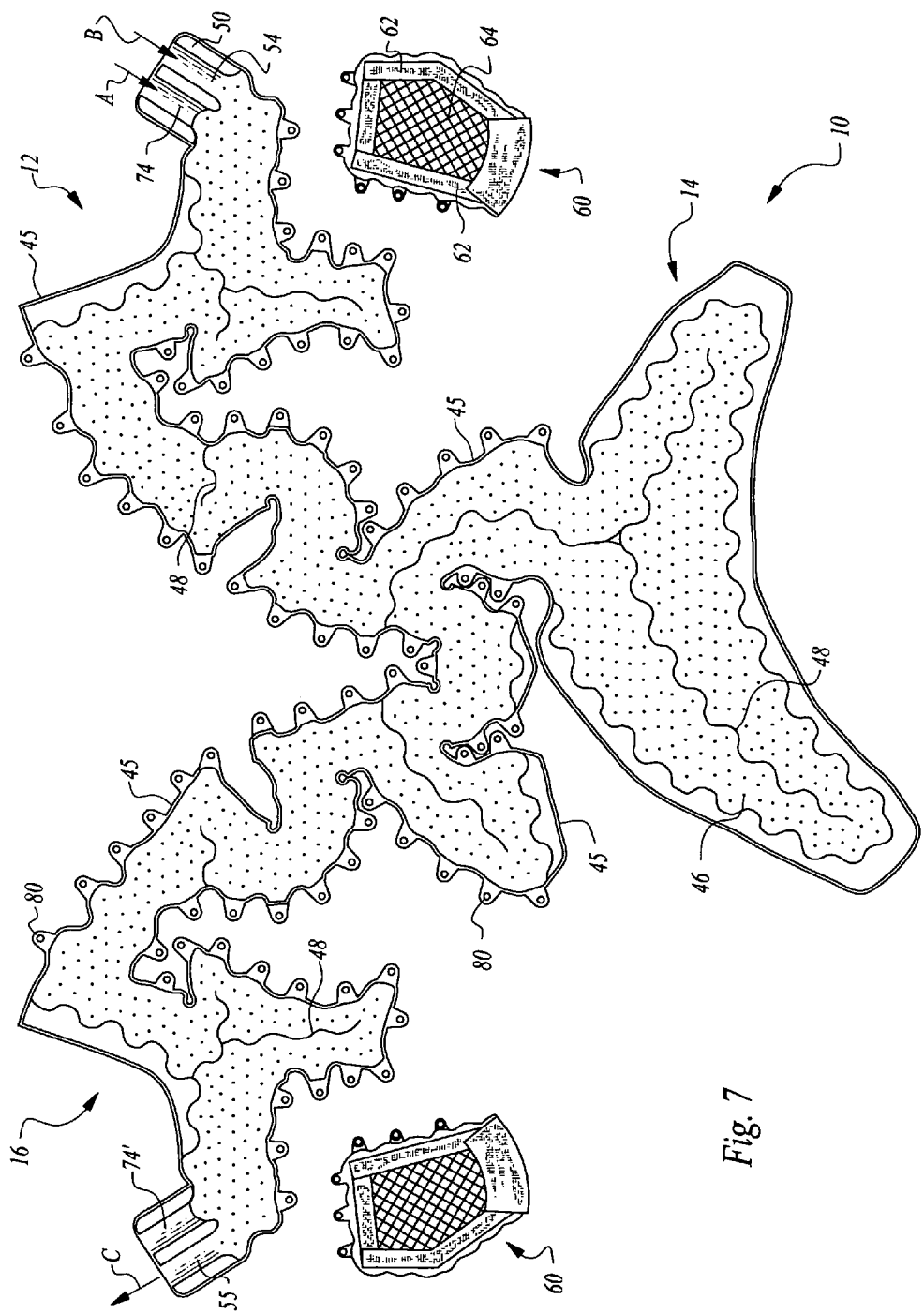
FIG. 7 is a full sectional laid flat view of the cap portion of the headliner of this invention with outer and mid layers of the cap removed and with an inner layer shown along with dots and fences, and indicating a pattern provided by the heat transfer fluid formed within the cap when laid flat.
Figure 15:
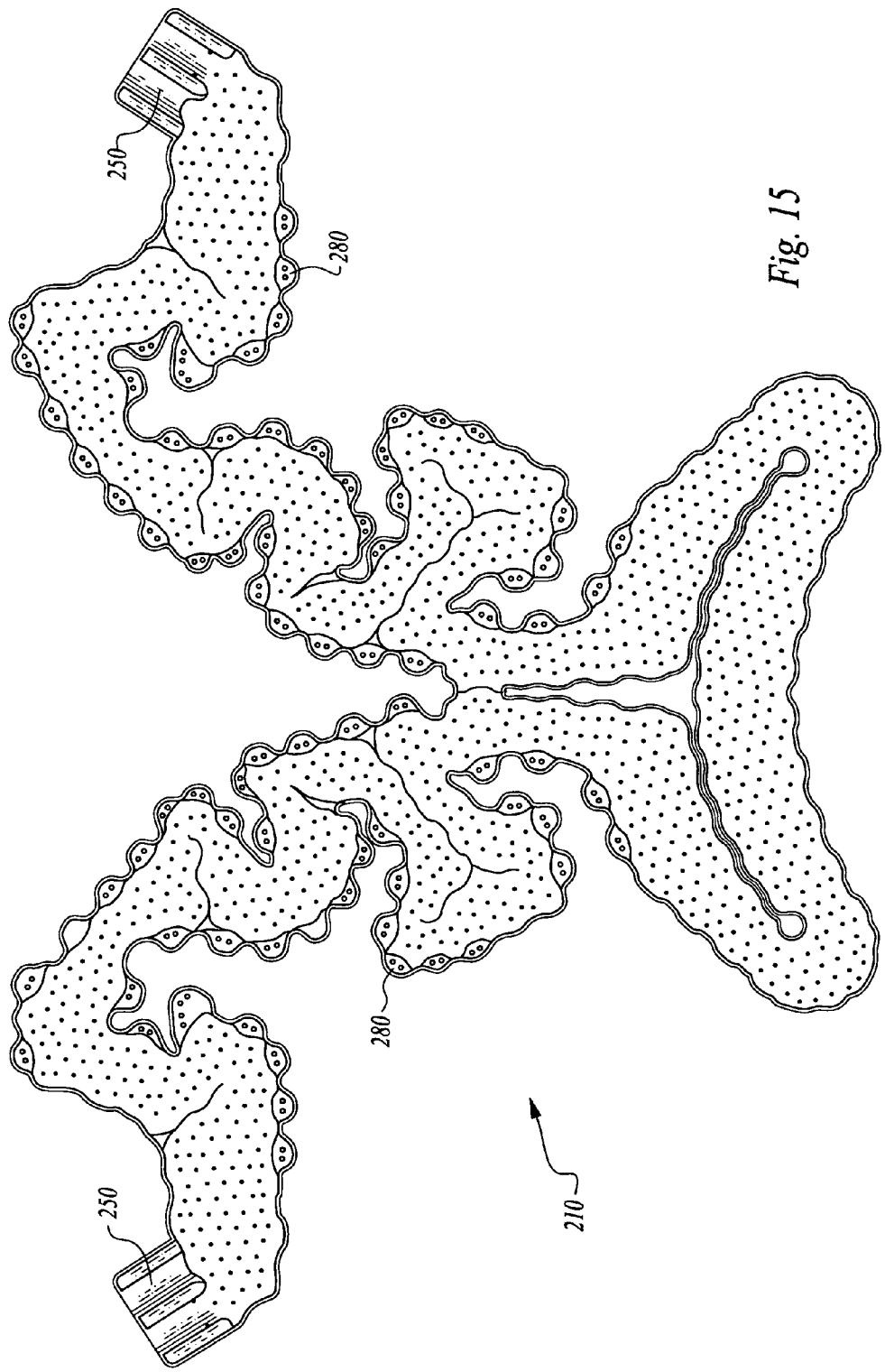

FIG. 15 is a laid flat top plan view of a further alternative embodiment of that which is shown in FIG. 7, and preferred for use with the integrated headliner and cervical collar of FIGS. 13 and 14.

Figure 16:
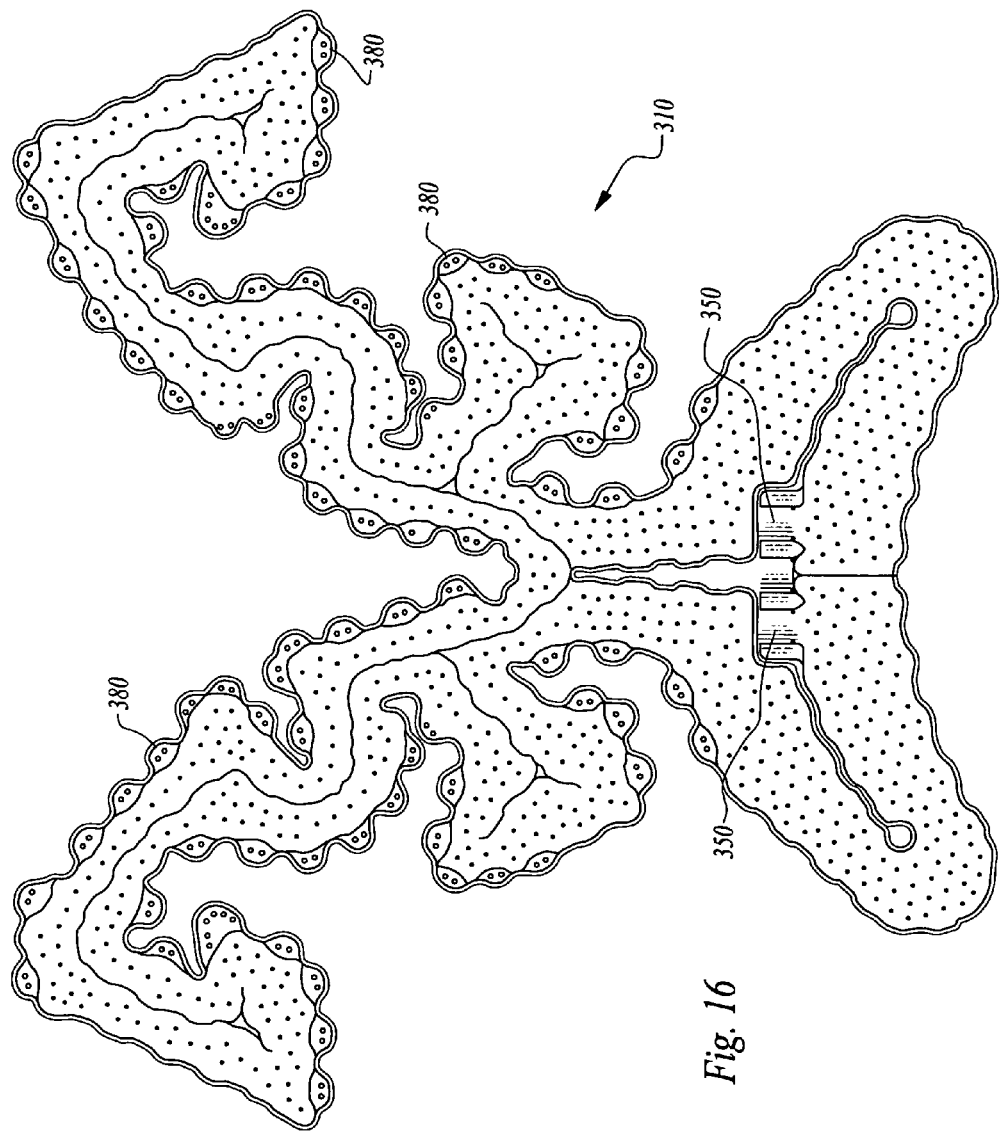

FIG. 16 is a laid flat top plan view of another alternative embodiment of the cap portion of FIG. 7.

Figure 17:
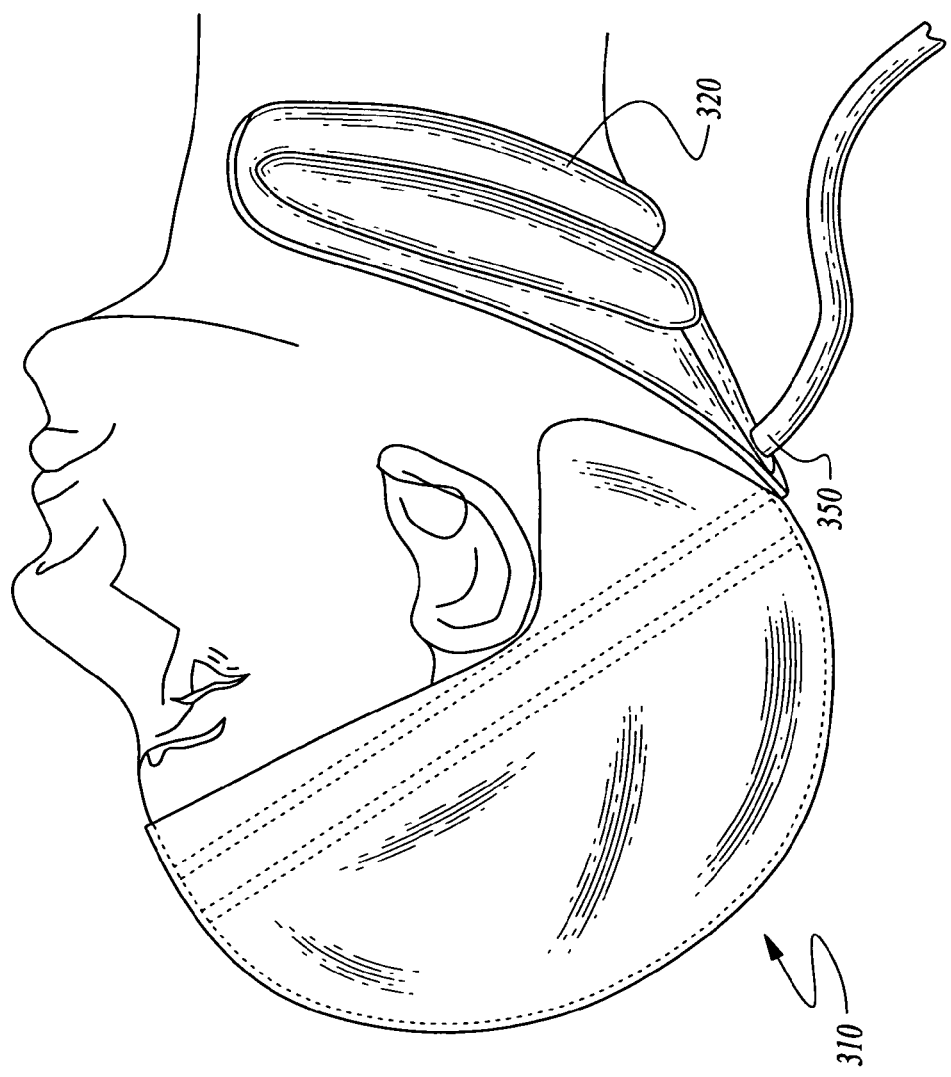

FIG. 17 is a side elevation view of the alternative embodiment of the cap portion of FIG. 16, and having a snap on collar, and viewed from the side of the patient wearing the headliner.

DETAILED DESCRIPTION OF THE PREFERRED EMBODIMENT

Referring to the drawings, wherein like reference numerals represent like parts throughout the various drawing figures, reference numeral 10 (FIG. 1) is directed to a cap portion of the temperature control headliner. The cap 10 is configured to be used within a temperature control system 100 (FIG. 12) to control (and typically reduce) a temperature of a head of a patient or other wearer. The headliner assembly preferably additionally includes a neck brace 20 (FIGS. 1 and 3) so that the headliner system can simultaneously control head temperature and provide cervical support, especially when the system is used in response to head trauma.

Figure 1:
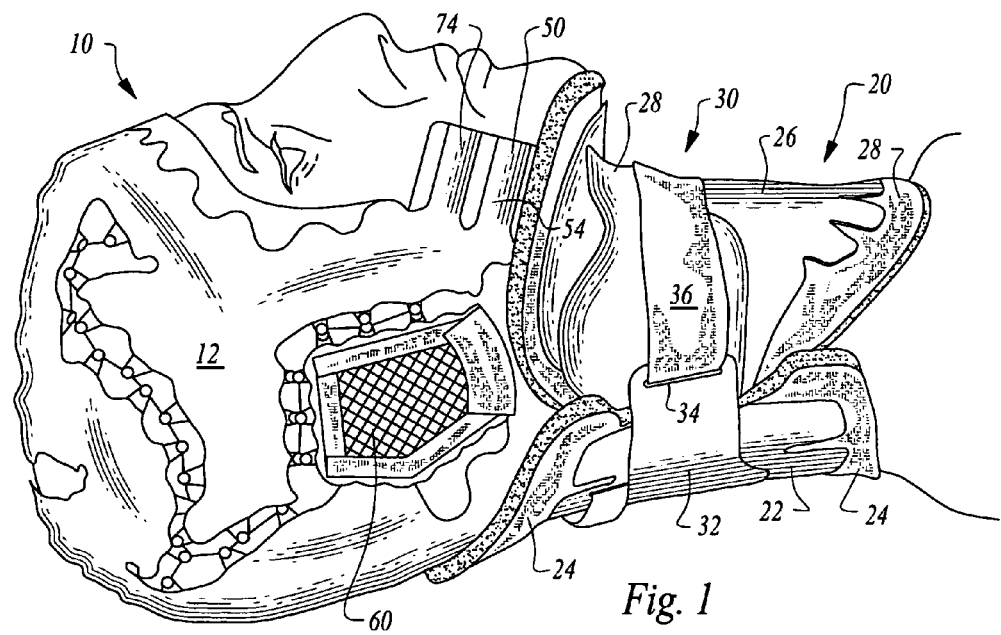
FIG. 1 is a side elevation view of the cap and neck brace portions of the headliner of this invention viewed from a side of a patient wearing the headliner.
Figure 2:
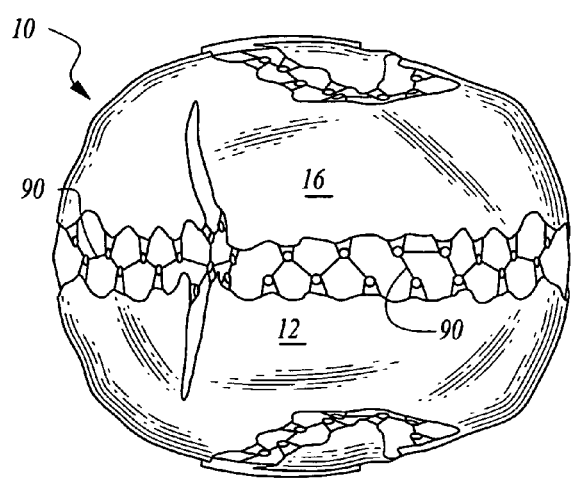
FIG. 2 is an end elevation view of that which is shown in FIG. 1.
Figure 9:
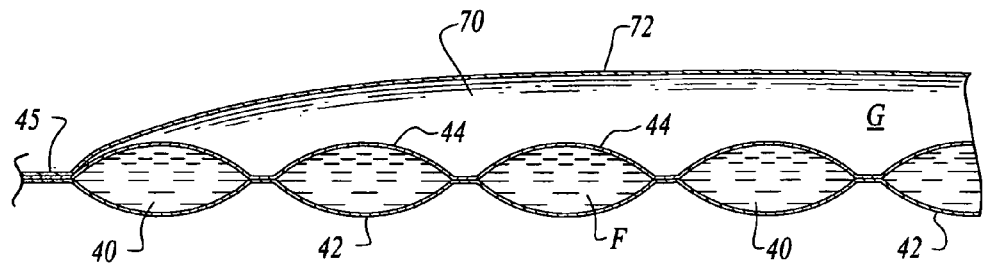
FIG. 9 is a full sectional view of a portion of the cap of this invention illustrating the relative orientation of the air bladder and fluid space of the cap portion of the headliner of this invention.

In essence, and with particular reference to FIGS. 1, 7 and 9, basic details of the headliner system of the preferred embodiment, including the cap 10 and the neck brace 20, are described. The cap 10 is sized and shaped to fit snugly over the head of a patient, except leaving the face of the patient typically exposed. A heat transfer fluid pathway is routed through the cap 10 with the fluid pathway in heat transfer relationship with the head of the patient. Preferably, the neck brace 20 is included with the cap 10 to form the headliner of this invention. The neck brace 20 and cap 10 of the cooling headliner are synergistically integrated to both accelerate the time when cooling can begin and stabilize the cap 10 of the headliner with a minimum of time and effort. The neck brace 20 surrounds the neck of the patient and provides for neck support, particularly in circumstances where a neck injury may have occurred. A strap 30 is provided with the neck brace 20 to secure the neck brace 20 in position. Preferably, a neck portion 14 (FIG. 7) of the cap 10 is configured to be placed on a lower rear portion of the head of the patient, and down partially onto an upper portion of the neck of the patient. The neck brace 20 thus holds this neck portion 14 against the head of the patient.

With reference to FIG. 9, a cross-section of a portion of the cap 10 shows a fluid space 40 within the fluid pathway filled with the heat transfer fluid F. This fluid space 40 is placed directly adjacent the head of the patient for heat transfer between the heat transfer fluid F within the fluid space 40 and the head of the patient. With reference to FIG. 7, an inlet 50 is provided where the heat transfer fluid enters the fluid pathway within the cap 10. This inlet 50 extends along the fluid pathway within the cap 10 to an outlet 55. Ear covers 60 are optionally provided to help in proper positioning of the cap 10, to provide some measure of protection for ears of the patient, and to still allow the patient to hear. However, because of integration to the cervical collar, no ear covers are required. Eliminating the ear covers 60 allows medical access to the ears without removing the assembly. An air bladder 70 (FIG. 9) preferably overlies the fluid space 40 within the cap 10. The air bladder 70 is filled with an elevated pressure gas G which helps to cause the fluid space 40 to be in intimate contact with the head of the patient, for maximum heat transfer therebetween. The pathways within the cap 10 are preferably bordered by a plurality of tabs 80 which are coupled together by cords 90. The cords 90 are preferably elastic to allow the cap 10 to stretch somewhat so that the cap 10 can fit snugly over patients having different head sizes. To avoid skin irritation, a series of small holes extend around the headliner. These holes only exist in the outermost layer of the assembly so that the elastic cord is not forced onto the skin to eliminate skin irritation.

Figure 12:
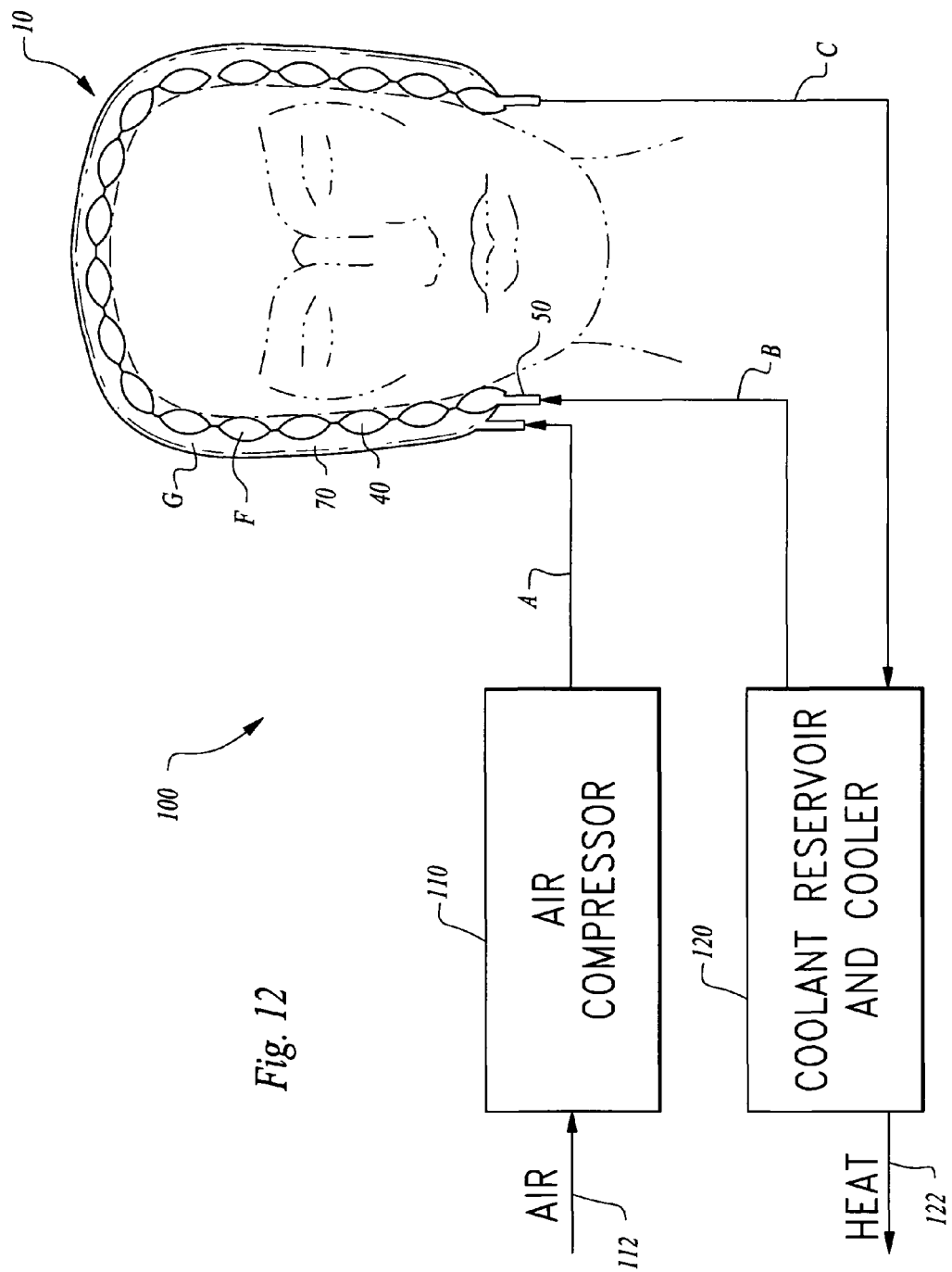
FIG. 12 is a schematic depicting an overall temperature control system for a patient's head, utilizing the headliner of this invention.

The overall headliner assembly including the cap 10 and the neck brace 20 is preferably included within a head temperature control system 100 (FIG. 12). This system 100 is intimately integrated into the headliner and includes an air compressor 110 for supplying compressed air to the air bladder 70. A coolant reservoir and cooler 120 is also provided to cool the heat transfer fluid and to cause the heat transfer fluid F (FIG. 9) to be recirculated between the inlet 50 and outlet 55 (FIG. 7).

More specifically, and with particular reference to FIGS. 4-7, details of the general configuration of the cap 10 are described. The cap 10 has two different orientations including a somewhat spherical orientation (FIGS. 1-6) when the cap 10 is ready to be placed over a head of a patient, and a flat orientation which the cap 10 would exhibit if not laced up by the cords 90 and if allowed to lay flat, as the cap 10 is originally manufactured (FIG. 7). The neck portion of the headliner is intimately attached to the cervical collar to create simultaneous fixing of both elements to the patient's head. The cap portion of the headliner is preferably contained in a throw-away envelope secured to the rear and above the cervical collar. Once the collar is secured the envelope is opened and the remainder of the headliner is secured to the patient's head. The cap is ready to apply with the elastic lacing in place. A combining of both components in the invention both increases safety for the injured patient by first securing the collar and accelerates when cooling begins. The cap 10 includes a heat transfer fluid pathway therein extending between the inlet 50 and the outlet 55 (FIG. 7). The heat transfer fluid F (FIG. 9) enters the inlet 50 along arrow B and passes amongst dots 46 and between fences 48 (described in detail below) to travel through all portions of the fluid pathway within the cap 10, until the fluid F arrives at the outlet 55 and exits the cap 10, along arrow C. These pathways within the cap 10 are generally symmetrical, so that the inlet 50 and outlet 55 can be swapped if desired. Thus, the cap 10 includes a right half 12 and a left half 16 which are generally similar to each other. The cap 10 also includes a neck portion 14 generally between the right half 12 and the left half 16. When the cap 10 is laced together with the cords 90, the cap 10 takes on a semi-spherical form, similar to that depicted in FIGS. 4-6.

Figure 3:
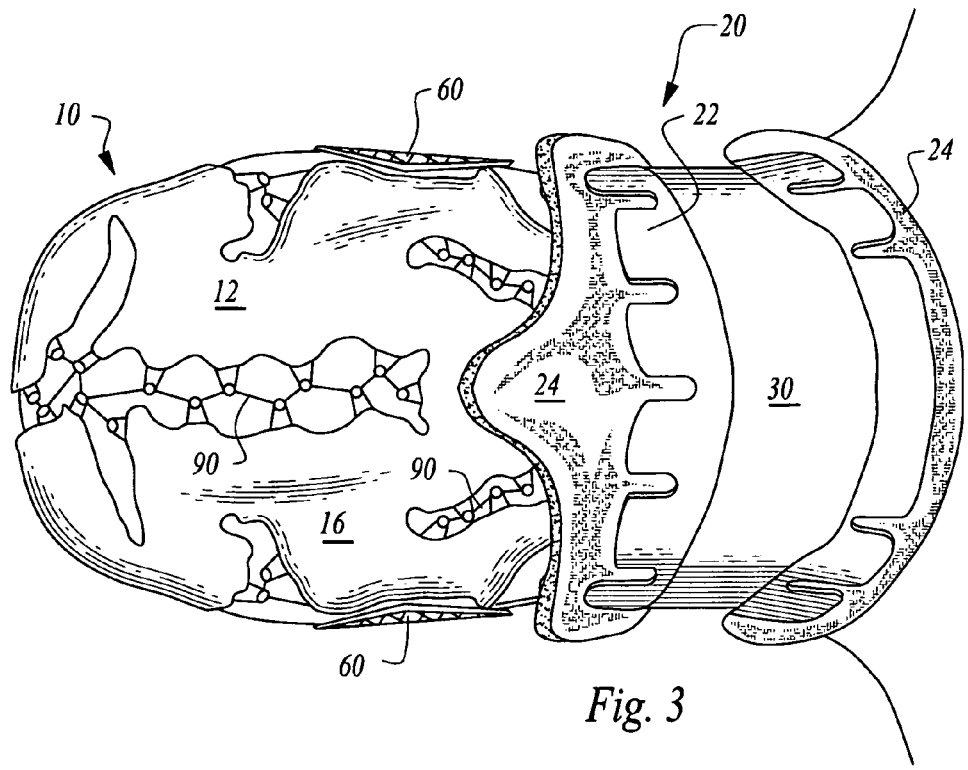
FIG. 3 is a bottom plan view of that which is shown in FIG. 1.

With particular reference to FIGS. 1 and 3, details of the neck brace 20 are described. The neck brace 20 is preferably an Aspen Vista Collar supplied by Aspen Medical Products, Inc. of Irvine, Calif. and modified to integrate with the neck element of the headliner. The securing of the neck cooling element is eliminated by physically securing the neck cooling element. In particular, the neck brace 20 preferably includes an at least semi-rigid rear shell 22 with rear foam 24 inboard of the rear shell 22 for direct neck contact. A front shell 26 of semi-rigid form is provided with front foam 28 for direct skin contact. The rear shell 22 and front shell 26 together surround the neck of the patient.

A strap 30 is provided to secure the shells 22, 26 together. The neck brace 20 can optionally include a gap within the front shell 26 to facilitate performance of a tracheotomy procedure. While this preferred form of neck brace 20 is described and shown, the cap 10 could be utilized without the neck brace 20, or with some other form of neck brace if desired. The neck brace 20 beneficially supports the neck of the patient, particularly where a head trauma event has occurred and it is unclear or known that a neck injury has occurred. The neck brace 20 additionally overlies at least a portion of the cap 10, and particularly the neck portion 14, so that the headliner of this invention cools the upper portions of the neck, as well as the head of the patient.

The strap 30 (FIG. 1) includes a rear support 32 with a slit 34 therein. A front length 36 of strap material is fixed to the rear shell 22 on the left side of the brace and is fed through the slit 34 and preferably secures back to itself or to other portions of the rear shell 22, such as through utilization of velcro or other fasteners, so that the strap 30 secures the front shell 26 and rear shell 22 together.

Most preferably, the cap 10 and neck brace 20 are attached together and provided as a single assembly. In deployment of this assembly, the neck brace 20 would be put in place first with the cap 10 folded against an upper portion of the rear shell 22. After the neck brace 20 has been properly located and secured with the strap 30, the cap 10 portion would be unfolded and stretched over the head of the patient. After the cap 10 is in position, then appropriate heat transfer fluid conduits are connected to the inlet 50 and outlet 55 so that circulation of the heat transfer fluid can commence.

With particular reference to FIGS. 7 and 9-11, further details of the cross-section and interior structure of the cap 10 and included heat transfer fluid pathways are described. The cap 10 preferably is formed of three layers of fluid impervious flexible material, such as a flexible plastic material capable of having structures attached thereto through techniques such as radio frequency (RF) bonding. A fluid space 40 for the heat transfer fluid F is provided between an inner layer 42 and a mid layer 44. The inner layer 42 is adapted to be located directly adjacent the head of the patient. The mid layer 44 is on a side of the inner layer 42 further from the patient than the inner layer 42, when the cap 10 is in position upon the head of the wearer.

A border 45 defines a region where the inner layer 42 and mid layer 44 are secured together along with the outer layer 42 defining the air bladder 70. This border 45 is also that portion of the cap 10 which includes the tabs 80 thereon which support the cord 90 (described in detail below). The heat transfer fluid pathway generally extends between opposite borders within the cap 10. However, dots 46 and fences 48 are also located between the borders 45. Dots 45 define points which have had the inner layer 42 and mid layer 44 bonded together. These dots 46 help to encourage heat transfer fluid F flow throughout the entire surface area covered by the heat transfer fluid pathway, and encourage mixing of the heat transfer fluid to maintain uniform temperature. The dots 46 also help to maintain the heat transfer fluid pathway as a thin fluid space 40 so that the heat transfer fluid F remains close to the head of the patient. The fences 48 help to route the heat transfer fluid F to all of the portions of the heat transfer fluid pathway within the cap 10.

The dots 46 are preferably substantially round, but could be square, rectangular or exhibit other faceted or curved forms, being primarily non-elongate, but rather mostly residing near a central point. The dots 46 are preferably substantially uniformly spaced from each other and occupy a generally hexagonal pattern with the dots 46 adjacent a central dot 46 spaced about sixty degrees from each other. The dot 46 spacing is most preferably 0.32 inches, and configured to cause the inner layer 42 and mid layer 44 of the cap 10 to be spaced <0.10 inches from each other. The dot spacing is preferably optimized to account for various parameters including the peel strength of the material, the operating pressure of the fluid in the garment, the weight and volume of the heat transfer fluid, the skin thermal conductance, and the ratio of dot area to conductance area. In some instances, these parameters can dictate dot 46 spacing of 0.30 inches or less or 0.35 inches or more. The cap 10 layer spacing can conceivably increase in some instances to 0.15 inches or even 0.20 inches or more under some conditions.

The fences 48 thus act similar to the border 45, but between the borders 45. Most preferably, these fences 48 only extend between the inner layer 42 and mid layer 44, with the air bladder 70 extending between the borders 45 and over the fences 48.

The fences 48 preferably are aligned with the dots 46 such that no dots 46 are close to the fences 48, but so that the fences 48 are either generally a maximum distance away from the dots 46 or intersect the dots 46. Following such criteria, the fences 48 have a generally highly irregular serpentine configuration. The fences 48 are similarly formed by bonding the inner layer and the outer layer together, such as by radio frequency radiation bonding together.

A careful review of FIG. 7 shows that some portions of the heat transfer fluid pathway between the inlet 50 and the outlet 55 inside the cap 10 do not include fences therein, but rather have a width defined by a distance between opposite borders 45. In other regions, fences 48 are provided so that the heat transfer fluid F (FIG. 9) must find the appropriate path by going around the fences 48, thus causing the heat transfer fluid F to pass through all of the different portions of the cap 10 and to maximize effective heat transfer between the heat transfer fluid F and the head of the patient.

The inlet 50 is preferably in the form of a generally cylindrical receiver 54. This receiver 54 is adapted to receive at least a portion of a porting tube 52 (FIG. 4) therein. The porting tube 52 can include valves and disconnect structures to allow the cap 10 to be connected and disconnected to other portions of the temperature control system 100 (FIG. 12). The outlet 55 is preferably configured similar to the inlet 50, so that the inlet 50 and outlet 55 can be swapped. For instance, if a medical care provider determines that one side of a head of a patient is in greater need of cooling than another side, then the supply of coolant would be directed to the right half 12 or left half 16 which needs cooling most urgently. Thus, the coolest heat transfer fluid F would be delivered where the need is greatest for cooling.

Figure 4:
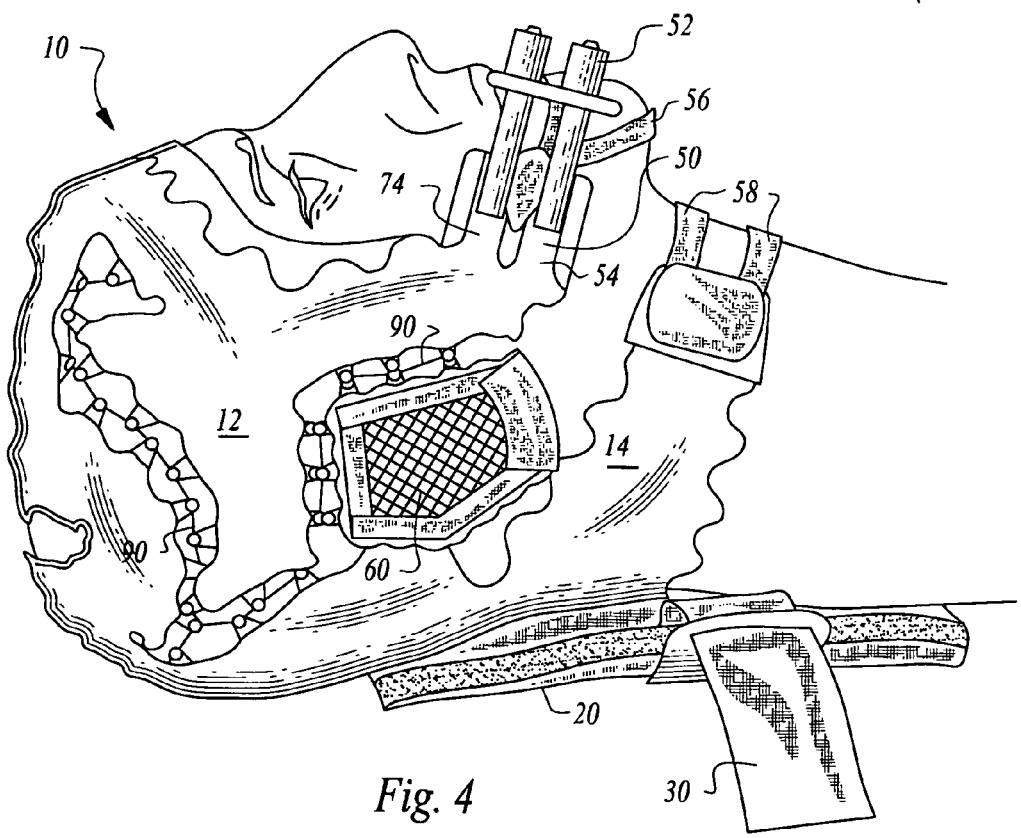
FIG. 4 is a side elevation view of that which is shown in FIG. 1 with portions of the neck brace removed to reveal details of the cap beneath the neck brace portion of the headliner of this invention.
Figure 5:
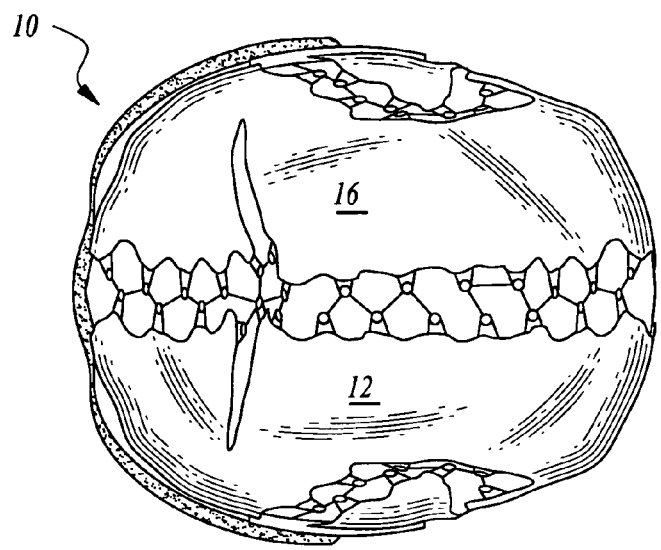
FIG. 5 is an end elevation view of that which is shown in FIG. 4.
Figure 6:
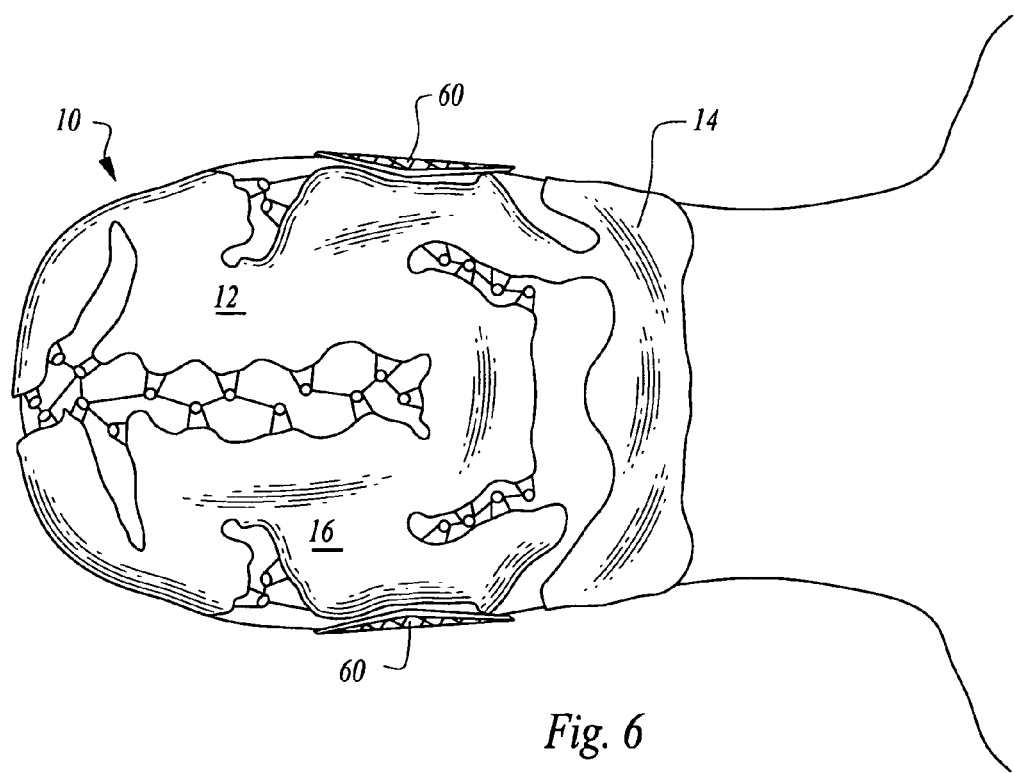
FIG. 6 is a bottom plan view of that which is shown in FIG. 4.

The portions of the cap 10 near the inlet 50 and outlet 55 optionally but preferably include a chin strap 56 (FIG. 4) so that these portions of the cap 10 remain adjacent cheeks of the patient. The chin strap 56 preferably extends between the left half 16 and right half 12, and can be removably attachable, such as during deployment of the cap 10, or can be continuous and merely stretched as the cap 10 is stretched and deployed over the head of the patient. A neck strap 58 (FIG. 4) is optionally additionally provided to hold the neck portion 14 (FIG. 7) adjacent the lower head and upper neck portion of the patient (FIG. 4). This neck strap 58 preferably has two straps with a gap therebetween to facilitate performance of a tracheotomy procedure therebetween. These neck straps 58 are preferably removably attachable and become more optional when the neck brace 20 is in position to hold the neck portion 14 securely in place.

The ear covers 60 are preferably connected to the cap 10 through utilization of the cords 90 and tabs 80 similar to coupling of various portions of the cap 10 to each other. The ear covers 60 include a border 62 with the mesh 64 therein which covers an outer surface of the ear. The border 62 supports the tabs for connecting to the cap 10.

The cap 10 also includes an air bladder 70 overlying the fluid space 40 within the cap 10 (FIG. 9). In FIGS. 1-6, the outermost surface of portions of the cap 10 including the right half 12, neck portion 14 and left half 16 actually show the outer layer 72 of the cap 10 which overlies the air bladder 70. While the air bladder 70 preferably does not include the dots 46 and fences 48 (FIGS. 9-11), the air bladder 70 could optionally include dots 46 and fences 48 similar to that provided within the fluid space 40. As an other alternative, the air bladder 70 could be provided with its own inner and outer layers and be generally continuous and provided as a second garment overlying a first garment forming the fluid space 40. In FIG. 7, the outer layer 72 and the mid layer 44 have been removed so that the air bladder 70 is not in place and so that the particular position of the dots 46 and fences 48 can be more completely shown.

The air bladder 70 includes an entrance 74 preferably adjacent the inlet 50 and adapted to couple to a portion of the porting tubes 52. This entrance 74 can then be coupled to an air compressor 110 of the temperature control system 100 (FIG. 12). It is not strictly required that the air bladder 70 remain coupled to a source of compressed air. Rather, it can be filled with pressurized air, or other gas G, and then sealed off with the pressure remaining to beneficially force the heat transfer fluid F within the fluid space 40 against the head of the patient.

Figure 10:
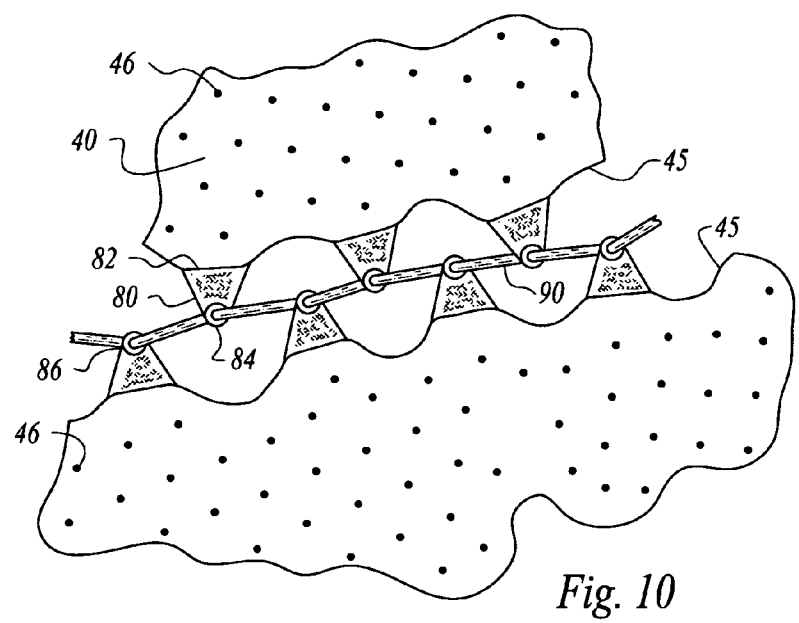
FIG. 10 is a detail of a portion of that which is shown in FIGS. 1-6 revealing how the elastic cord joins portions of the cap together through tabs with eyelets therein.
Figure 11:
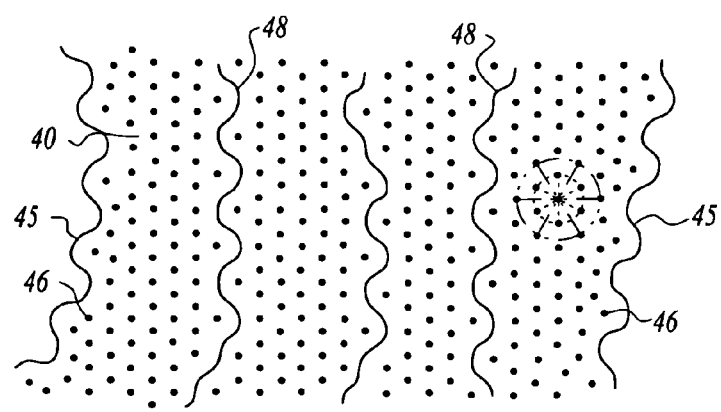
FIG. 11 is a schematic further illustrating details of the dots and fences provided according to this invention.

With particular reference to FIG. 10, particular details of the tabs 80 and cord 90 for securing various portions of the cap 10 to each other, are described according to a preferred embodiment. The tabs 80 each include a base 82 coupled to the border 45 along a side of the fluid space 40 (FIG. 7). The tabs 80 extend from this base 82 to a tip 84 spaced from the base 82. An eyelet 86 passes through the tip 84. The eyelet 86 is sized to receive the cord 90 therethrough. Most preferably, the cord 90 is both flexible and elastic, with the cord still being somewhat effective without exhibiting elasticity. When the cord 90 is elastic, the cap 10 has a greater degree of size adjustability to fit patients with heads of different sizes. The cord 90 is threaded through the eyelets 86 of the tabs 80 in various different fashions so that the tabs 80 and associated borders 45 are secured together.

With particular reference to FIG. 12, details of the overall temperature control system 100 and use of this invention are described. Initially, a patient who is believed to have experienced a brain injury and would benefit from head temperature reduction, or other wearers who require head temperature modification are identified. In the case of head trauma, the neck brace 20 is first secured about a neck of the patient. Next, the cap 10 is stretched over the patient's head and deployed, as shown in FIG. 1. Finally, the porting tubes 52 are utilized to connect the inlet 50 and outlet 55 to other portions of the system 100.

In particular, an air compressor 110 is provided which receives air 112 or some other gas G, and compresses it and delivers it, along airflow path A, into the entrance 74 (FIG. 7) or alternative entrance 74', for filling the air bladder 70 with the gas G, such as air. This coupling procedure also couples a coolant reservoir 120 with cooler to the inlet 50 for the heat transfer fluid F to be delivered into the fluid space 40. Once connected, coolant in the form of heat transfer fluid F is delivered, such as with a pump therein, from the reservoir 120 along arrow B to the inlet 50. The heat transfer fluid F then passes through the fluid space 40 within the fluid pathways inside the cap 10, until the heat transfer fluid arrives at the outlet 55. Heat transfer fluid F will have increased in temperature as it has received heat from the patient's head. This warm fluid F is then returned, along arrow C, back to the coolant reservoir 120.

Coolant reservoir 120 preferably includes a cooler for removing heat 122 from the heat transfer fluid F before the heat transfer fluid F is allowed to return back to the fluid space 40 within the cap 10. Optionally, thermostatic control can also be provided with the reservoir and cooler so that medical professionals can control a degree of cooling which occurs. It is also conceivable that the system 100 of this invention could be used for temperature increase, such as in the case of hypothermia, to provide controlled temperature increase to a patient's head.

Figure 8:
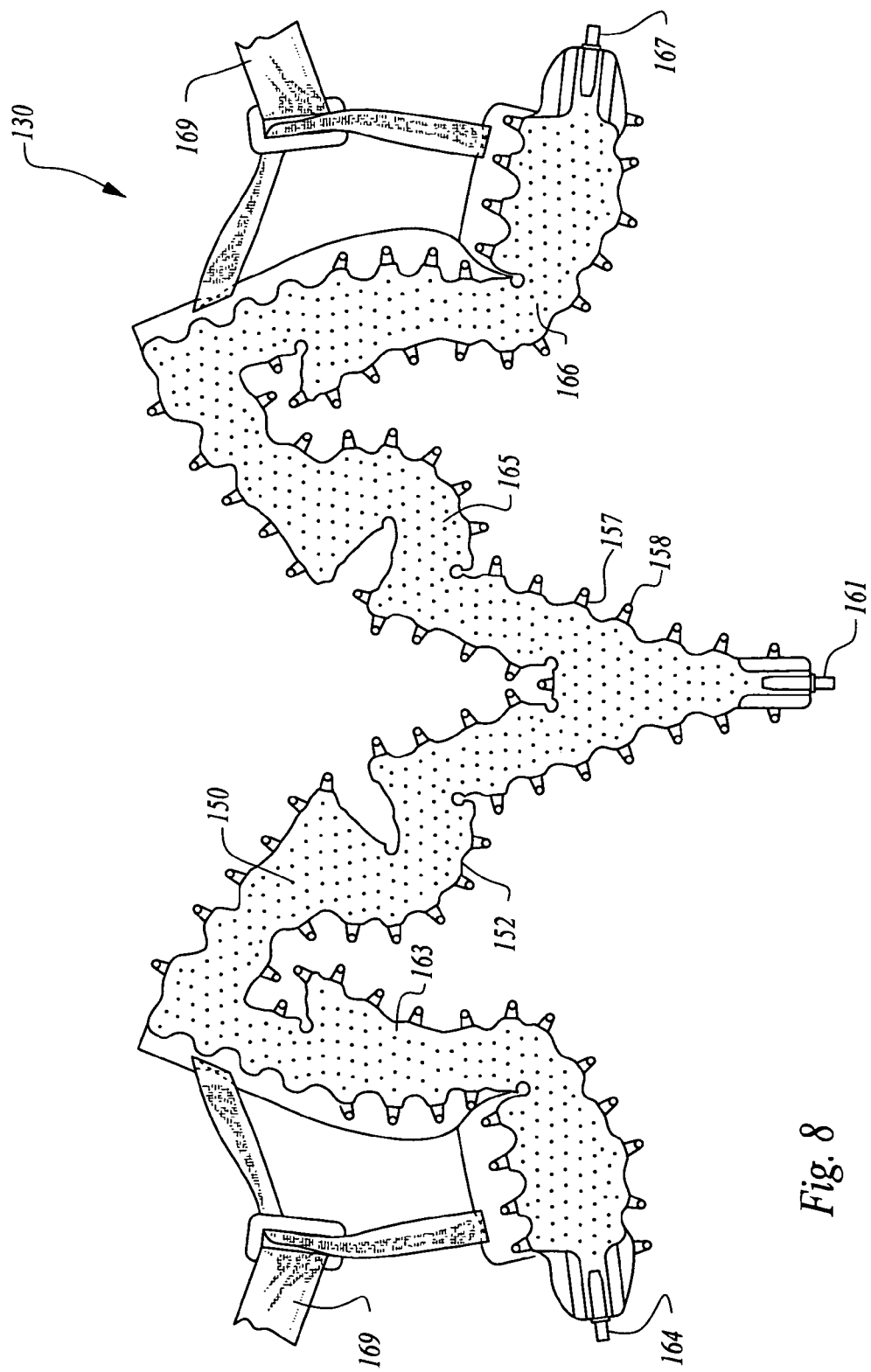
FIG. 8 is a laid flat view of an alternative embodiment of that which is shown in FIG. 7.

With particular reference to FIG. 8, an alternative cap 130 is described. The cap 130 provides a heat transfer garment which is particularly configured to remove heat from the head of the wearer and into the heat transfer fluid for cooling of the head of the wearer. The cap 130 preferably includes layering and dots 150 similar to those described above with regard to the cap 10. However, the cap 130 preferably does not include fences, but rather relies on having an elongate shape defined by borders 152.

In particular, the cap 130 preferably includes an inlet 161 which is adapted to be coupled to the cap 130 supply tube 145. Heat transfer fluid pathways within the cap 130 include a left forward path 162 which extends from a base of the skull of the head of the wearer when the cap 130 is on the head of the wearer toward a crown of the head. After reaching the crown, the left forward path 162 transitions into a left return path 163 which generally curves around the left ear on the head of the wearer and terminates at a left outlet 164 on a left side of the base of the head, adjacent the inlet 161.

Similarly, a right forward path 165 is provided extending forward and then connecting to a right return path 166 which extends back to a right outlet 167. The right forward path 165, right return path 166 and right outlet 167 are preferably substantially mirror images of the left forward path 162, left return path 163 and left outlet 164.

Tabs, eyelets and laces are preferably provided similar to those described above with regard to the cap 10, so that the paths 162, 163, 165, 166 of the cap 130 can be drawn tightly together and so that these paths 162, 163, 165, 166 take on a generally spherical form adapted to fit snugly over the head of the wearer. The left outlet 164 and right outlet 167 feed into a "Y" tube where fluid flow from these two outlets 164, 167 join together before the fluid is directed back to the cooler 120.

Most preferably, ear covers are also provided with tabs and eyelets so that they can be laced to the cap 130 and assist in securing the cap 130 securely to the head of the wearer. These ear covers with chin straps extend under the chin of the wearer.

With particular reference to FIGS. 13 and 14, side elevation views of a patient wearing the headliner with integrated cervical collar are shown in a modified embodiment of the headliner of this invention. In FIG. 13 a cap portion 210 is shown without the cervical collar portion. Note that neck sections of the cap portion 210 have been augmented to provide better cooling to the neck area, relative to other embodiments. As shown in FIG. 14, the cervical collar brace 220 overlies these neck sections almost entirely. The ear covers are dispensed with and ears fit between connections of the cap portion 210.

A cheek strap 260 is optionally provided adjacent each side of the cap 210 to secure the cap 210 directly to the neck brace/cervical collar 220. The cap portion 210 is also more symmetrical and tabs 280 are provided with a low profile form and holes to minimize irritation. Also, each tab 280 preferably has two holes to facilitate additional placing arrangements and to minimize a degree to which the laces 290 need to go between the head of the patient and the cap portion 210, but rather can thread into a hole, below the tab 280 and then up through the second hole and the laces 290 are always on an upper side of the tab 280 as they extend across to other cap 210 locations.

This cap portion 210 is symmetrical with an inlet 250 adjacent one cheek and an outlet adjacent the other cheek or with dual inlets adjacent one cheek and dual outlets adjacent the other cheek, or with both an inlet and an outlet at one of the two cheeks, but with an overall degree of cooling balanced for various different portions of the head of the patient.

With particular reference to FIG. 15, an alternative and most preferred configuration for the cap 210 is shown in a flattened top plan view thereof. The collar portion is designed to be more conformal to the neck and the lacing tabs 280 are shown generally with a pair of holes per lacing tab 280, but with certain lacing tabs having more holes therein.

The cooling-compression neck-head cooling device is physically secured to the cervical collar 220. The cranial portion of the head cooling device (i.e. the cap 210) can be packaged in an envelope at the rear of the cervical collar 220. Once the cervical collar 220 is secured and the patient's head and neck are stabilized, the envelope is opened and disposed of and the cap portion 210 is secured to the patient's head, such as by first expanding the laces 290 and then tightening the laces 290 as needed to adjust for the size of the patient's head.

The laces 290 can be formed of elastic material so that the overall cap portion 210 can be stretched to a larger size, fitted over the head of the patient, and then snap into position. Alternatively, the laces 290 can be tightened by applying tension to the laces and drawing various sections of the cap portion 210 tightly together over the patient's head.

The cap portion 210 can be further secured by utilizing the cheek strap 260 to secure the cap portion 210 adjacent the inlet 250 directly to the neck brace 220. Note that while the inlet 250 is shown, typically multiple access ports would be provided with one being an inlet and one being an outlet. A secondary port is also provided which is coupleable to a source of compressed air which fills a jacket outboard of the fluid containing layer (see FIG. 12). In FIGS. 13 and 14 this compressed air containing layer is removed to more clearly show the coolant containing layer of this invention.

In the embodiment depicted in FIGS. 13-15, separate ports are provided adjacent each cheek of the patient. One of these inlets 250 can be for inputting of coolant into the cap portion 210 and the other can be provided for removal thereof. If desired, an additional fence can be provided to split the entire pathway between the inlets 250 (FIG. 15) into two separate paths with the flow occurring in opposite directions along these two paths, such that a uniform distribution of heat transfer is provided throughout the cap portion 210.

With particular reference to FIGS. 16 and 17, details of a further alternative cap portion 310 are described. In FIG. 16 a top plan view of the cap portion 310 is shown laid flat. Note in particular that with this further alternative cap portion 310, a rear inlet 350 is provided which provides a distinct location for inputting and outputting of coolant fluid. This input output location for the rear inlet 350 is also depicted in FIG. 17. In FIG. 17 the outer air containing layer is shown and the coolant fluid containing layer is thus concealed.

With this further alternative cap portion 310, a snap-on collar 320 is provided which snaps on to a head of the patient from the rear. Resilient arms snap around a neck of the patient. Inboard of these resilient arms the neck girding sections of the cap portion 310 are provided which are adjacent the two rear inlets 350. These inlets 350 provide for input and output of heat transfer fluid into the cap portion 310. Tabs 380 are strategically located as in other embodiments to coact with laces for loosening and tightening of the cap portion 310 when being placed on or removed from a patient's head.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for controlling the temperature of a patient's head, the system comprising:
   a source of heat transfer fluid; and
   a cap,
      said cap having a flexible and foldable cap portion being of a size to fit over the head of the patient leaving the face of the patent exposed,
      said cap portion being configurable in a first orientation in which said cap portion is unfolded and allowed to lay flat, said cap portion being configurable in a second orientation in which said cap portion is arranged in a shape to fit over at least a portion of the head of a patient and to cover a majority of the surface of the head of the patient other than the face of the patient, and
      said cap portion having a fluid pathway with at least one inlet and at least one outlet, said at least one inlet coupled to said source of heat transfer fluid, said at least one outlet disposed upstream from said at least one inlet, and said fluid pathway extending between said at least one inlet and said at least one outlet,
      said fluid pathway located in a heat transfer relationship with at least a portion of the head of the patient when said cap portion is in said second orientation adjacent the head of the patient; and
   wherein said heat transfer fluid has a different temperature than the head of the patient, such that heat is transferred between the heat transfer fluid and the head of the patient.

2. The system of claim 1 wherein said heat transfer fluid from said source of heat transfer fluid is adapted to be cooler than a temperature of the head of the patient.

3. The system of claim 2 wherein said source of heat transfer fluid includes a heat transfer fluid cooler, said cooler including a return located downstream from said fluid pathway of said cap, said cooler adapted to cool the heat transfer fluid before recirculating the heat transfer fluid back to said inlet.

4. The system of claim 1 wherein said cap includes an air bladder overlying at least a portion of said fluid pathway with said air bladder on a side of said fluid pathway opposite a side of said fluid pathway adapted to be located adjacent the patient's head, said air bladder adapted to be filled with an elevated pressure gas, such that said air bladder increases a degree of surface contact between said fluid pathway and the head of the patient.

5. The system of claim 4 wherein said air bladder is adapted to be coupled to an air compressor at least temporarily for filling of said air bladder with compressed air.

6. The system of claim 4 wherein said cap includes at least three layers including an inner layer and a mid layer, with said fluid pathway located between said inner layer and said mid layer, and an outer layer with said air bladder located between said mid layer and said outer layer.

7. The system of claim 6 wherein a plurality of dots are provided extending between said inner layer and said mid layer with said fluid pathway routed around said dots.

8. The system of claim 7 wherein said fluid pathway includes a plurality of fences therein, said fences extending between said inner layer and said mid layer, said fences adapted to preclude heat transfer fluid passage therethrough, such that said fences direct the heat transfer fluid along said fluid pathway and between said inlet and said outlet.

9. The system of claim 8 wherein said fluid pathway passes along both a left side of the patient's head and a right side of the head of the patient, as well as adjacent at least a portion of the patient's neck as said fluid pathway extends between said inlet and said outlet.

10. The system of claim 9 wherein a neck brace portion is provided overlying and physically attached to said cap at a portion of said cap adapted to be located adjacent the neck of the patient, said neck brace adapted to surround the neck of the patient and provide cervical support for the neck of the patient.

11. The system of claim 9 wherein said fluid pathway is oriented between borders on either side of said fluid pathway extending between said inlet and said outlet, said borders defining a location where said inner layer, said mid layer and said outer layer are all joined together.

12. The system of claim 11 wherein a plurality of tabs are provided extending from said borders, each said tab including at least one eyelet at a tip of said tab opposite where said tab attaches to said border, and with at least one cord is routed through at least some of said eyelets of said tabs, such that said cords hold said tabs together to keep said fluid pathway in a shape tending to cover a majority of a surface of the patient's head other than the face of the patient.

13. The system of claim 12 wherein said cords are elastic in nature, such that said cap is caused to be elastically held to the head of the patient and to allow for said cap to fit securely on heads of different sizes.

14. The system of claim 1 wherein a plurality of dots are provided extending between an inner layer of said cap and a mid layer of said cap with said fluid pathway routed around said dots.

15. The system of claim 1 wherein said fluid pathway includes a plurality of fences therein, said fences extending between an inner layer of said cap and a mid layer of said cap, said fences adapted to preclude heat transfer fluid passage therethrough, such that said fences direct the heat transfer fluid along said fluid pathway and between said inlet and said outlet.

16. A system for controlling the temperature of the head of a patient, the system comprising:
   a source of heat transfer fluid;
   a neck brace; and
   a cap, said cap having:
      (a) a flexible and foldable cap portion being of a size to fit over at least a portion of the head of the patient leaving the face of the patient exposed;
      (b) a neck portion being configured to be placed on the lower rear portion of the head of the patent;
      (c) a fluid pathway with at least one inlet and at least one outlet, said at least one inlet coupled to said source of heat transfer fluid, said at least one outlet disposed upstream from said at least one inlet, said fluid pathway extending between said at least one inlet and said at least one outlet, said fluid pathway located in a heat transfer relationship with at least a portion of the head of the patient when said cap portion is adjacent the head of the patient; and
   wherein said neck brace is configured to surround the neck of the patient and to hold said neck portion of said cap against the head of the patient; and wherein said heat transfer fluid has a different temperature than the head of the patient, such that heat is transferred between the heat transfer fluid and the head of the patient.

17. The system of claim 16 wherein said neck portion of said cap is attached to said neck brace to allow for the simultaneous fixing of both said neck portion and said neck brace to the head of the patient.

18. The system of claim 17 and wherein said cap is configurable in a folded configuration in which said cap is folded; and further including an envelope secured to the rear of said neck brace and being of a size for containing said cap portion when said cap portion is in said folded configuration.

19. The system of claim 18 wherein said envelope is a throw-away envelope.

* * * * *